US008685412B2

(12) United States Patent
Huang et al.

(10) Patent No.: US 8,685,412 B2

(45) **Date of Patent: *Apr. 1, 2014**

(54) HEMORRHAGIC FELINE CALICIVIRUS, CALICIVIRUS VACCINE AND METHOD FOR PREVENTING DEVELOPMENT OF CALICIVIRUS DISEASE

(75) Inventors: Chengjin Huang, Fort Dodge, IA (US); Jennifer Hess, Fort Dodge, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 3 days.

This patent is subject to a terminal disclaimer.

(21) Appl. No.: 13/226,685

(22) Filed: Sep. 7, 2011

(65) Prior Publication Data

US 2011/0318383 A1 Dec. 29, 2011

Related U.S. Application Data

(60) Continuation of application No. 11/985,696, filed on Nov. 16, 2007, now abandoned, which is a division of application No. 11/223,099, filed on Sep. 9, 2005, now Pat. No. 7,306,807.

(60) Provisional application No. 60/609,480, filed on Sep. 13, 2004.

(51) Int. Cl.

*A01N 63/02* (2006.01)
*A61K 39/00* (2006.01)
*A61K 39/125* (2006.01)
*C12N 7/04* (2006.01)

(52) U.S. Cl.

USPC .................... 424/216.1; 424/184.1; 424/93.6; 435/236

(58) Field of Classification Search

None

See application file for complete search history.

(56) References Cited

U.S. PATENT DOCUMENTS

| | | | |
|---|---|---|---|
| 3,944,469 | A | 3/1976 | Bittle et al. |
| 4,264,587 | A | 4/1981 | Pedersen et al. |
| 4,522,810 | A | 6/1985 | Pedersen |
| 5,106,619 | A | 4/1992 | Wiesehahn et al. |
| 5,242,686 | A | 9/1993 | Chu et al. |
| 5,374,424 | A | 12/1994 | Kelsey et al. |
| 5,972,350 | A | 10/1999 | Atherton et al. |
| 6,004,563 | A | 12/1999 | Chu et al. |
| 6,051,239 | A | 4/2000 | Simpson et al. |
| 6,231,863 | B1 | 5/2001 | Colau et al. |
| 6,355,246 | B1 | 3/2002 | Kruger et al. |
| 7,306,807 | B2 | 12/2007 | Huang et al. |
| 2004/0180064 | A1 | 9/2004 | Foley et al. |
| 2004/0259225 | A1 | 12/2004 | Foley et al. |

FOREIGN PATENT DOCUMENTS

WO WO-2006 031795 3/2006

OTHER PUBLICATIONS

Radford et al., Veterinary Microbiology, 2006, 117:14-18.*

Radford et al., Vet. Res., 2007, 38:319-335.*

Pedersen et al., "Mechanisms for persistence of acute and chronic feline calicivirus infections in the face of vaccination," Vet. Microbiol. 47(1-2):141-156 (Nov. 1995).

Pedersen et al., "An isolated epizootic of hemorrhagic-like fever in cats caused by a novel and highly virulent strain of feline calicivirus," Vet. Microbiol.73:281-300 (May 2000).

Schorr-Evans et al., "An epizootic of highly virulent feline calicivirus disease in a hospital setting in New England," Journal of Feline Medicine and Surgery 5.217-226 (2003).

Lauritzen et al., "Serological analysis of feline calicivirus isolates from the United States and United Kingdom," Veterinary Microbiol. 56(1-2):55-63 (May 1997).

Hohdatsu et al., "Neutralizing feature of commercially available feline calicivirus (FCV) vaccine immune sera against FCV field isolates," J. Vet. Med. Sci. 61(3):299-301 (Mar. 1999).

Radford et al., "Comparison of serological and sequence-based methods for typing feline calcivirus isolates from vaccine failures," Vet. Rec. 146(5):117-123 (Jan. 29, 2000).

Davis et al., "Studies on the safety and efficacy of an intranasal feline rhinotracheitis-calici virus vaccine," VM-SAC 71:1405-1410 (Oct. 1976).

Kahn et al., "Induction of immunity to feline caliciviral disease," Infect. Immun. 11:1003-1009 (May 1975).

Kahn, "Feline viruses: pathogenesis of picornavirus infection in the cat," Am. J. Vet. Research 32:521-531 (Apr. 1971).

Hurley et al., "An Outbreak of virulent systemic feline calicivirus disease," J. Am. Vet. Med. Assoc. 224(2):241-249 (Jan. 15, 2004).

Van Maanen et al., "Viral Haemorrhagic Disease: a review and personal experience," Tijdschr. Voor Diergeneeskunde, Apr. 1996, vol. 121, No. 7, pp. 184-188 [Engl. summary on p. 184].

Mia et al., "Feline Leukemia," Kleintier-Praxis 1983, vol. 28, No. 5, pp. 247-256 [Engl. summary on p. 253].

International Search Report and Written Opinion for PCT/US2005/032528 dated May 16, 2006.

(Continued)

*Primary Examiner* — Nicole Kinsey White

(74) *Attorney, Agent, or Firm* — Michael P. Morris; Joyce L. Morrison

(57) ABSTRACT

The present invention relates to a novel, isolated and purified hemorrhagic feline calicivirus FCV-DD1. The invention further embraces monovalent and multivalent vaccines containing the new FCV-DD1 strain. In addition, the invention encompasses methods of protecting felines against infection or preventing disease caused by feline calicivirus alone or in addition to other pathogens that comprises administering to the felines an immunologically effective amount of the monovalent and multivalent vaccines described herein. Also, the invention concerns methods for diagnosing or detecting the hemorrhagic feline calicivirus in a susceptible host, asymptomatic carrier and the like by detecting the presence of feline calicivirus FCV-DD1 or antibodies raised or produced against feline calicivirus FCV-DD1 antigen.

34 Claims, No Drawings

(56) References Cited

OTHER PUBLICATIONS

Radford et al., "The capsid gene of feline calicivirus contains linear B-cell epitope in both variable and conserved regions," Journal of Virology, Oct. 1999, vol. 73, No. 10, pp. 8496-8502.

Radford et al., "The use of sequence analysis of a feline calicivirus (FCV) hypervariable region of the epidemiological investigation of FCV related diseases and vaccine failures," Vaccine, 1997, vol. 15, No. 12-13, pp. 1451-1458.

Seal et al., "Analysis of feline calicivirus capsid protein genes: identification of variable antigenic determinant regions of the protein," Journal of General Virology, 1993, vol. 74, pp. 2519-2524.

Tohya et al., "Mapping of Antigenic Sites Involved in Neutralization on the Capsid Protein of Feline Calicivirus", Journal of General Virology, vol. 78 (1997), pp. 303-305.

* cited by examiner

HEMORRHAGIC FELINE CALICIVIRUS, CALICIVIRUS VACCINE AND METHOD FOR PREVENTING DEVELOPMENT OF CALICIVIRUS DISEASE

CROSS-REFERENCE TO RELATED U.S. APPLICATIONS

This application is a continuation of application Ser. No. 11/985,696, filed Nov. 16, 2007, now abandoned which is a divisional of application Ser. No. 11/223,099, filed Sep. 9, 2005, now U.S. Pat. No. 7,306,807, which claims the benefit under 35 U.S.C. 119€ of U.S. Provisional application No. 60/609,480, filed Sep. 13, 2004, now abandoned. The prior applications are incorporated herein by reference in their entirety.

STATEMENT REGARDING FEDERALLY SPONSORED RESEARCH OR DEVELOPMENT

Not Applicable

REFERENCE TO A "SEQUENCE LISTING"

Not Applicable

BACKGROUND OF THE INVENTION

1. Field of the Invention

The present invention concerns a new isolated and purified strain of virulent, hemorrhagic feline calicivirus, vaccines produced therefrom and the use of the vaccines to protect cats from calicivirus infection or disease.

2. Description of the Related Art

All patents and publications cited in this specification are hereby incorporated by reference thereto in their entirety.

Feline calicivirus (FCV) often causes an acute crisis in multiple-cat environments, particularly animal hospitals and, to a lesser extent, animal shelters. Typically, the FCV infection presents signs resembling viral rhinotracheitis (FVR) by affecting the upper respiratory tract and, on occasion, producing joint pain and lameness. Additionally, the infected cat will develop ulcers on the tongue and in the mouth region. Vesicles and erosions of the nasal passages, the hard palate and the tongue appear prevalent. Other symptoms of FCV disease include high fever, hair loss, skin ulcerations and edema (swelling) in the legs or around the face. Depending on the virulence of the infecting strain, the FCV infection may become fatal. The primary method of transmission is through the oral route of infection but cats can also get the infection from inhalation of infectious virus found in the saliva, feces or urine of infected cats.

The FCV infection can affect both domestic cats and some wild feline species. Since FVR and FCV comprise almost 90% of all feline respiratory infections, the availability of effective vaccines to prevent these two diseases is of great significance. FCV is a single-stranded RNA virus capable of mutating into new strains (J. N. Burroughs et al., "Physiochemical evidence for the re-classification of the caliciviruses," Journal Gen. Virol. 22:281-286 (1974)). Over sixty-five feline caliciviruses exist worldwide, which makes adequate protection by vaccination using a singly comprised vaccine largely incomplete and difficult. Because the virus is capable of mutation, monovalent vaccines based on a single strain of FCV may not be sufficiently protective against other FCV strains (see, generally, N. C. Pedersen et al., "Mechanisms for persistence of acute and chronic feline calicivirus infections in the face of vaccination," Veterinary Microbiol. 47(1-2):141-156 (November 1995); A. Lauritzen et al., "Serological analysis of feline calicivirus isolates from the United States and United Kingdom," Veterinary Microbiol. 56(1-2):55-63 (May 1997); T. Hobdatsu et al., "Neutralizing feature of commercially available feline calicivirus (FCV) vaccine immune sera against FCV field isolates," Journal of Veterinary Medicine Sci., 613:299-301 (March 1999); A. D. Radford et al., "Comparison of serological and sequence-based methods for typing feline calcivirus isolates from vaccine failures," Vet. Rec. 146(5):117-123 (Jan. 29, 2000)).

Another problem with FCV is that the virus is highly contagious, infected cats will continue to shed the virus for long periods of time after infection and recovered cats may remain lifelong carriers of the infectious virus. Asymptomatic cats can even spread fatal disease to other healthy cats. Recent outbreaks have been reported in Northern California and New England of two genetically diverse strains of highly virulent, hemorrhagic calicivirus that were particularly fatal to the feline population in animal shelters, named FCV-Ari and FCV-Diva, respectively (N. C. Pedersen et al., "An isolated epizootic of hemorrhagic-like fever in cats caused by a novel and highly virulent strain of feline calicivirus," Veterinary Microbiol. 73:281-300 (May 2000); E. M. Schorr-Evans et al., An epizootic of highly virulent feline calicivirus disease in a hospital setting in New England," Journal of Feline Medicine and Surgery 5:217-226 (2003)).

In the past, monovalent viral vaccines have been described and several manufactured to prevent feline diseases using a variety of antigens such as the feline calicivirus F9 strain (U.S. Pat. No. 3,944,469 (J. L. Bittle et al.)), feline *Chlamydia psittaci* (U.S. Pat. Nos. 5,972,350 and 5,242,686 (H.-J. Chu at al)), feline leukemia virus (U.S. Pat. No. 4,264,587 (N. C. Pedersen et al)) and the like. Other calicivirus strains such as the FCV-M8 and FCV-255 and feline rhinotracheitis virus have also been previously isolated and described for vaccine use (E. V, Davis et al., "Studies on the safety and efficacy of an intranasal feline rhinotracheitis-calici virus vaccine." VM-SAC 71:1405-1410 (1976); D. E. Kahn et al., "Induction of immunity to feline caliciviral disease," Infect. Immun. 11:1003-1009 (1975); D. E. Kahn, "Feline viruses: pathogenesis of picornavirus infection in the cat," Am. J. Vet. Research 32:521-531 (1971)). Further, U.S. Pat. No. 4,522,810 (N. C. Pedersen) describes a feline calicivirus vaccine that contains the FCV-2280 strain. U.S. Pat. No. 6,231,863 (D. Colau et al.) describes nucleotide sequences from the genome of the FCV-2280 strain and vaccines using the nucleotide sequences of the capsid gene for preventing feline calicivirus disease. U.S. Pat. No. 5,106,619 (G. P. Wiesehahn et al.) discloses the preparation of inactivated viral vaccines that include feline calicivirus among others. U.S. Pat. No. 6,051,239 (L. Simpson et al.) describes oral vaccines that use a modified botulinum toxin in conjunction with antigens such as the calicivirus.

More recently, a strain of FCV-Kaos was identified (K. F. Hurley et al, "An Outbreak of virulent systemic feline calicivirus disease, J. Am. Vet. Med. Assoc. 224(2):241-249 (Jan. 15, 2004)) and, subsequently, both FCV-Kaos and FCV-Ari strains were isolated (U.S. Patent Application No. 20040180064 A1, Hemorrhagic feline calicivirus, pub. Sep. 16, 2004). The isolated virulent systemic calicivirus (VS-FCV) strains, including FCV-Kaos, FCV-Ari and FCV-Bellingham, have been described as comprising a capsid protein including an amino acid residue selected from the group consisting of lysine (K) at amino acid position 448; glutamic acid (E) at amino acid position 452; lysine (K) at amino acid position 581; and aspartic acid (D) at amino acid position 581

(U.S. Patent Application No. 20040259225 A1, Virulent systemic feline calicivirus, pub. Dec. 23, 2004).

Multivalent vaccines have been prepared or described to contain mixtures of many viral antigens such as *Chlamydophila felis* (formerly known as feline *Chlamydia psittaci*) in combination with one or more pathogens comprising feline leukemia virus, feline panleukopenia virus, feline calicivirus, feline rhinotracheitis virus, feline acquired immunodeficiency virus, rabies, feline infectious peritonitis, *Borrelia burgdorferi* and the like (U.S. Pat. No. 6,004,563 (H.-J Chu et al.)). Another mixture of Rickard isolate feline leukemia virus, feline rhinotracheitis virus, feline calicivirus and feline panleukemia virus has similarly been disclosed as a vaccine (U.S. Pat. No. 5,374,424 (W. H. Kelsey et al.)).

Unfortunately, none of the prior vaccines that contain previously used strains of the feline calicivirus adequately protect the feline from the emerging hemorrhagic feline calicivirus strains. In the recent hemorrhagic feline calicivirus outbreaks, there were a significant number of deaths despite the fact that the cats had received vaccinations against the calicivirus.

As a consequence, there is a definite art-recognized need in the veterinary field to produce an efficacious, safe vaccine against the highly virulent, hemorrhagic feline calicivirus infections. Another art-recognized need is to provide a broad-spectrum viral vaccine that protects cats against serious infection and disease caused by both hemorrhagic and common FCV strains. The novel FCV strain of the present invention is able to satisfy those needs by uniquely and advantageously eliciting specific immune response against the virulent, hemorrhagic strain of FCV to protect cats from acute and chronic viral disease. In combination with common calicivirus strains, the new FCV strain of this invention is able to achieve excellent virus-neutralizing antibody titers and make broad-spectrum immunization possible.

BRIEF SUMMARY OF THE INVENTION

The present invention concerns a highly infectious, novel hemorrhagic FCV strain, designated FCV-DD1, which is useful as a vaccine strain. A further embodiment of the invention is drawn to new methods of using the vaccine to immunize cats against infection and disease caused by the hemorrhagic feline calicivirus. Also embraced by this invention are methods for diagnosing or detecting the hemorrhagic feline calicivirus in a susceptible host, asymptomatic carrier and the like by detecting the presence of feline calicivirus FCV-DD1 or antibodies raised or produced against feline calicivirus FCV-DD1 antigen.

BRIEF DESCRIPTION OF THE SEVERAL VIEWS OF THE DRAWINGS

Not Applicable

DETAILED DESCRIPTION OF THE INVENTION

In accordance with the present invention, there is provided a new, highly infectious strain of feline calicivirus (FCV) and veterinary vaccines to protect cats from viral infection caused by the calicivirus. More specifically, the invention describes an isolated and purified hemorrhagic feline calicivirus "FCV-DD1" and includes the viral clones derived from the FCV-DD1 isolate. (Whenever the FCV-DD1 isolate is mentioned herein, it is understood that the viral clones may substitute for the parent isolate in each instance.) Also described are vaccines containing an immunogenic amount of FCV-DD1 and methods of protecting felines against infection or preventing disease caused by feline calicivirus that comprises administering to the feline in need of protection an immunologically effective amount of the vaccine. The vaccine may optionally contain one or more additional FCV isolates such as, for example, FCV-255, FCV-2280, FCV-Diva, FCV-Kaos, FCV-Bellingham, FCV-F9, FCV-F4, FCV-M8, etc. Desirably, the vaccine will contain FCV-DD1 together with FCV-255, FCV-2280 or both, and, more preferably, the mixture of FCV-DD1 with FCV-255.

Also, the vaccine may optionally contain other antigens or pathogens such as *Chlamydophila felis* (*C. felis*), feline leukemia virus (FeLV), feline panleukopenia virus (FPV), feline rhinotracheitis virus (FVR), feline immunodeficiency virus, rabies virus, feline infectious peritonitis virus, *Bartonella* bacteria (e.g. typical cat scratch disease), a combination thereof and the like. Preferably, the mixture of antigens comprises FCV-DD1 in combination with *C. felis*, feline leukemia virus, feline panleukopenia virus and feline rhinotracheitis virus or in combination with *C. felis*, feline panleukopenia virus and feline rhinotracheitis virus. A particularly preferred multivalent vaccine comprises FCV-DD1, a non-hemorrhagic feline calicivirus such as FCV-255, feline rhinotracheitis virus and feline panleukopenia virus, with the optional addition of feline leukemia virus and/or *C. felis*, or other FCV strains.

Leading up to the discovery of the new hemorrhagic feline calicivirus FCV-DD1 strain, a tissue culture sample of FCV-Ari was obtained from Dr. Neils Pedersen at the School of Veterinary Medicine, UC Davis, California (N. C. Pedersen et al., "An isolated epizootic of hemorrhagic-like fever in cats caused by a novel and highly virulent strain of feline calicivirus," Veterinary Microbiol. 73:281-300 (May 2000)). The sample of FCV-Ari was frozen, thawed and used to infect a tissue culture roller bottle of confluent Crandell Feline Kidney Cells (CRFK) (R. A. Crandell et al, "Development, characterization, and viral susceptibility of a feline (*Felis catus*) renal cell line (CRFK)," *In Vitro* 9:176-185 (1973)). Later, the roller bottle was frozen, thawed and the culture fluid was aliquoted as working stock.

The initial FCV-Ari "working stock" was used to inoculate cats in order to confirm that the "working stock" from the material received from Dr. Neils Pedersen contained hemorrhagic calicivirus. The cats inoculated with the FCV-Ari "working stock" elicited extreme clinical signs such as high temperatures, edema, dehydration, and death confirming that the FCV-Ari "working stock" contained hemorrhagic calicivirus.

The FCV-Ari "working stock" was then diluted to a titer of $10^5$ $TCID_{50}$ per mL, frozen, thawed, and 0.2 μm filtered. The filtered FCV-Ari was used for subsequent purification and isolation of the most virulent calicivirus strain. The filtered FCV-Ari was clarified, serially diluted and used to infect 24-well tissue culture plates confluent with CRFK cells. The well of the highest dilution which contained a cytopathic effect (CPE) on the CRFK cells was harvested, frozen, quick thawed, serially diluted, and used to infect another 24-well tissue culture plate confluent with CRFK cells. This procedure was repeated two times for a total of three rounds of purification and isolation.

A portion of the thus-purified FCV-Ari was formalin inactivated and used to blend a killed, monovalent vaccine. This inactivated FCV-Ari vaccine was injected into cats to measure the serological response to vaccination. Unexpectedly, the vaccine failed to induce virus-neutralizing antibody titers even though antibodies against the virus were induced as confirmed by ELISA. In addition, the purified FCV-Ari (live)

was used to inoculate two groups of cats. These two groups of cats exhibited no clinical signs characteristic of a hemorrhagic calicivirus infection such as high temperatures, edema, pyoderma, alopecia, etc. Because the killed vaccine did not induce neutralizing antibodies and the live stain purified from the "working stock" of FCV-Ari did not cause hemorrhagic calicivirus infection in a controlled challenge study, the isolated virus from the first purification of the sample of FCV-Ari was confirmed not to be the hemorrhagic isolate; further work and vaccine development of this strain ceased. It was then presumed that the original virus sample of FCV-Ari contained two FCV strains or possibly more, at least one of which was not virulent as demonstrated by the isolated strain that was obtained from the first purification.

In an attempt to isolate the virulent strain that caused hemorrhagic feline calicivirus infection, the original tissue culture sample of FCV-Ari was used for three rounds of purification and isolation. In order to accomplish the task, the FCV-Ari sample was incubated with the antisera generated from the original FCV-Ari (killed) vaccination. The virus was serially diluted and used to infect 24-well tissue culture plates confluent with CRFK cells, and the wells of the highest dilution which displayed a cytopathic effect (CPE) on the CRFK cells were harvested. The harvested virus clones were evaluated by standard serum virus-neutralization assays. Each viral clone was incubated with the antisera generated from the first purification killed vaccine, or with the antisera generated from challenge with the live "working stock." The results from this serum neutralization assay showed, surprisingly, that there was more than one strain of calicivirus in the original sample and further confirmed that the strain isolated from the first round of purification was not the hemorrhagic strain. The viral clones that were not selected and discarded were those that were neutralized by the antisera specific to the undesired product of the first purification. The virus clones selected for the subsequent rounds of purification were those that were neutralized by antisera to the original virus from Dr. Pedersen yet were not neutralized by antisera specific to the undesired product of the first purification. Virus clone selection by harvesting the highest dilution causing CPE was repeated for a total of three rounds. The resulting virus isolate, designated FCV-DD1, was inoculated into cats and the cats exhibited typical hemorrhagic calicivirus clinical signs. By this process, the purified and isolated FCV-DD1 stain was determined to be a true hemorrhagic feline calicivirus stain, previously unknown in the veterinary field.

Consequently, the new, purified and isolated FCV-DD1 strain, vaccines of FCV-DD1 and methods of using the calicivirus are included within the scope of the present invention. Inoculated cats are protected from serious viral infection and disease caused by the calicivirus. The novel method protects cats in need of protection against viral infection by administering to the cat an immunologically effective amount of a vaccine according to the invention, such as, for example, the vaccine containing killed, modified live or attenuated FCV-DD1 or its clone. The vaccines may further contain additional antigens to promote the immunological protection of cats against multiple feline diseases including, but not limited to, non-hemorrhagic calicivirus strains, e.g., FCV-255, FCV-2280, etc., other hemorrhagic calicivirus strains, e.g., FCV-Diva, FCV-Kaos, FCV-F9, etc. and other suitable antigens such as feline viral rhinotracheitis, feline panleukopenia virus (feline distemper), *Chlamydophila felis* (*C. felis*), etc. The additional antigens may be given concurrently to the cat in a combination product or separately in order to provide a broad spectrum of protection against viral infections. Most preferably, the mixture contains FCV-DD1, FCV-255, *C. felis*, feline leukemia virus, feline panleukopenia virus and feline rhinotracheitis virus or, alternatively, FCV-DD1, FCV-255, feline panleukopenia virus and feline rhinotracheitis virus, killed virus, and, optionally, feline leukemia virus and/or *C. felis* or other FCV strains. To broaden the scope of protection conferred by the FCV-DD1 containing vaccine against infection or disease in complementary fashion, it is helpful to have the multivalent vaccine contain two or more FCV strains in which the additional FCV strain may include, but is not limited to, FCV-255, FCV-2280, FCV-Diva, FCV-Kaos, FCV-Bellingham, FCV-F9, FCV-F4, FCV-M8, etc.; and it is particularly beneficial to include at least one or more non-hemorrhagic strain such as FCV-255, FCV-2280, etc. When certain FCV antigens such as FCV-F9 are employed, it is desirable to make a modified live or attenuated vaccine to accommodate the virulence of the virus. A preferred combination of antigens in a vaccine is one in which the additional feline calicivirus with FCV-DD1 comprises FCV-255, FCV-2280 or the combination of FCV-255 and FCV-2280, in conjunction with at least feline panleukopenia virus and feline rhinotracheitis virus.

The vaccines comprise, for example, the infectious viral strain as an inactivated (killed) virus, an attenuated virus, a modified live virus, etc. in combination with a nontoxic, physiologically acceptable carrier or diluent and other inert excipients, adjuvants or conventional co-formulants that are tolerated by the feline species. The isolated and purified FCV-DD1 strain or its viral clone can be used as a monovalent vaccine in which protection relies on its ability to provide protection against infection by other serotypes through cross-neutralization. Repeated inoculation with the same serotype typically confers protection against subsequent severe infection.

The new vaccines of this invention are not restricted to any particular type or method of preparation. The viral vaccines include, but are not limited to, inactivated (killed) vaccines, modified live vaccines, attenuated vaccines, attenuated vaccines, subunit vaccines, genetically engineered vaccines, etc. These vaccines are prepared by standard methods known in the art. The most preferred vaccines for delivery of the new FCV-DD1 strain to inoculate cats against the virulent FCV infection and disease are the inactivated (killed) or modified live virus vaccines.

To prepare inactivated virus vaccines, for instance, virus propagation is done by methods known in the art or described herein. Virus inactivation is achieved by protocols generally known to those of ordinary skill in the art. Inactivated virus vaccines may be prepared by treating the virus with inactivating agents such as formalin or hydrophobic solvents, acids, beta propiolactone, binary ethyleneimine, etc. Formalin is the most preferred inactivating agent. Inactivation is conducted in a manner understood in the art. For example, to achieve chemical inactivation, a suitable virus sample or serum sample containing the virus is treated for a sufficient length of time with a sufficient amount or concentration of inactivating agent at a sufficiently high or low temperature or pH, depending on the inactivating agent, to inactivate the virus. The virus is considered inactivated if it is unable to infect a cell susceptible to infection.

The preparation of submit vaccines typically differs from the preparation of a modified live vaccine or an inactivated vaccine. Prior to preparation of a subunit vaccine, the protective or antigenic components of the vaccine must be identified. Such protective or antigenic components include, for example, the immunogenic proteins or capsid proteins of the virus strain. These immunogenic components are identified by methods known in the art. Once identified, the protective or antigenic portions of the virus (i.e., the subunit) are subsequently purified by standard procedures and/or cloned by standard recombinant DNA techniques (see, for example, Maniatis et al., "Molecular Cloning: A Laboratory Manual," Cold Spring Harbor Laboratory, Cold Spring Harbor, Mass., 1989). The subunit vaccine provides an advantage over other vaccines based on the live virus since the subunit, such as highly purified subunits of the virus, is less toxic than the whole virus.

To prepare attenuated vaccines from virulent viral clones, the tissue culture adapted, live pathogenic FCV is first attenuated by methods known in the art, typically made by serial passage through cell cultures. Attenuation of pathogenic clones may also be made by introducing point mutations, effecting gene deletions in the virus genome.

An immunologically effective or immunogenic amount of the vaccine of the present invention is administered to a feline in need of protection against viral infection, usually 8 to 10 weeks of age or older. The immunologically effective or immunogenic amount that inoculates the cat against FCV infection and disease can be easily determined or readily titrated by routine testing by those of ordinary skill in the veterinary field. An effective amount is one in which a sufficient immunological response to the vaccine is attained to protect the cat exposed to the virulent feline virus. This immunological response for FCV is generally shown through the ability of the vaccine to induce virus-neutralizing antibody titers. Preferably, the cat is protected to an extent in which one to all of the adverse physiological symptoms or effects of the viral disease state are significantly reduced, ameliorated or totally prevented.

The vaccine is typically administered in a single dose or repeated dosages over time. Dosages range, for example, from about 0.25 mL to about 3.5 mL, usually about 0.5 mL to about 2.5 mL, preferably from about 0.8 mL to about 1.2 mL, and most preferably, at about 1.0 mL, depending upon the concentration of the immunogenic component of the vaccine, but should not contain an amount of virus-based antigen sufficient to result in an adverse reaction or physiological symptoms of viral infection. Methods are well known in the art for determining or titrating suitable dosages of active antigenic agent to find minimum effective dosages based on the weight of the cat, concentration of the antigen and other typical factors. For optimal immunization, a healthy cat is vaccinated with a dose of approximately 1 mL using aseptic technique and then a second 1 mL dose is given in about two to four weeks later. Annual revaccination with a single booster shot of the vaccine is useful to maintain good immunity against infection.

The vaccine can conveniently be administered intranasally, transdermally (i.e., applied on or at the skin surface for systemic absorption), parenterally, orally, etc., or a combination such as oronasal where part of the dose is given orally and part is given into the nostrils. The parenteral route of administration includes, but is not limited to, intramuscularly, subcutaneously, intradermally (i.e., injected or otherwise placed under the skin), intravenously and the like. The intramuscular, subcutaneous and oronasal routes of administration are most preferred.

When administered as a liquid, the present vaccine may be prepared in the conventional form of an aqueous solution, syrup, elixir, tincture and the like. Such formulations are known in the art and are typically prepared by dissolution or dispersion of the antigen and other additives in the appropriate carrier or solvent systems for administration to cats. Suitable nontoxic, physiologically acceptable carriers or solvents include, but are not limited to, water, saline, ethylene glycol, glycerol, etc. The vaccine may also be lyophilized or otherwise freeze-dried and then aseptically reconstituted or rehydrated using a suitable diluent shortly before use. Suitable diluents include, but are not limited to, saline, Eagle's minimum essential media and the like. Typical additives or co-formulants are, for example, certified dyes, flavors, sweeteners and one or more antimicrobial preservatives such as thimerosal (sodium ethylmercurithiosalicylate), neomycin, polymyxin B, amphotericin B and the like. Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions that contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of feline body fluids. Isotonicity can be appropriated adjusted with sodium chloride and other salts as necessary. At the time of vaccination, the virus is thawed (if frozen) or reconstituted (if lyophilized) with a physiologically-acceptable carrier such as deionized water, saline, phosphate buffered saline, or the like. Suitable solvents, such as propylene glycol, can be used to increase the solubility of the ingredients in the formulation and the stability of liquid preparations.

Further additives that may be employed in the present vaccine include, but are not limited to, dextrose, conventional antioxidants and conventional chelating agents, such as ethylenediamine tetraacetic acid (EDTA). Other pharmaceutically acceptable adjuvants that may optionally supplement the vaccine formulation include, but are not limited to, surfactants, polyanions, polycations, peptides, mineral oil emulsion, immunomodulators, a variety of combinations and the like. Further non-limiting examples of suitable adjuvants include squalane and squalene (or other oils of animal origin); polyoxyethylene-polyoxypropylene block copolymers such as Pluronic® (L121, for example, commercially available from BASF Aktiengesellschaft, Ludwigshafen, Germany); saponin; detergents such as Tween®-80 (polysorbate 80, commercially available from Sigma Chemical Co., St. Louis, Mo.); Quil A (commercial name of a purified form of *Quillaja saponaria*, available from Iscotec AB, Sweden and Superfos Biosector a/s, Vedback, Denmark); mineral oils such as Marcol® (a purified mixture of liquid saturated hydrocarbons, commercially available from ExxonMobil, Fairfax, Va.); vegetable oils such as peanut oil; *Corynebacterium*-derived adjuvants such as *Corynebacterium parvum; Propionibacterium*-derived adjuvants such as *Propionibacterium acne; Mycobacterium bovis* (Bacille Calmette-Guerin, or BCG); interleukins such as interleukin-2 and interleukin-12; interferons such as gamma interferon; combinations such as saponin-aluminum hydroxide or Quil A-aluminum hydroxide; liposomes; iscom adjuvant; mycobacterial cell wall extract; synthetic glycopeptides such as muramyl dipeptides or other derivatives; N,N-dioctadecyl-N,N'-bis(2-hydroxyethyl)-propanediamine (pyridine); Lipid A; dextran sulfate; DEAE-Dextran; carboxypolymethylene, such as Carbopol® (polyacrylic polymer commercially available from B.F. Goodrich Company, Cleveland, Ohio); ethylene maleic anhydride or ethylene/maleic anhydride copolymers (EMA®, a linear ethylene/maleic anhydride copolymer having approximately equal amounts of ethylene and maleic anhydride, having an estimated average molecular weight of about 75,000 to 100,000, commercially available from Monsanto Co., St. Louis, Mo.); acrylic copolymer emulsions such as a copolymer of styrene with a mixture of acrylic acid and methacrylic acid like NeoCryl® A640 (e.g. U.S. Pat. No. 5,047,238, an uncoalesced aqueous acrylic acid copolymer of acrylic acid and methacrylic acid mixed with styrene, commercially available from Polyvinyl Chemicals, Inc., Wilmington, Mass.); animal poxvirus proteins; subviral particle adjuvants such as orbivirus; cholera toxin; dimethyldioctadecylammonium bromide (DDA, commercially available from Kodak, Rochester, N.Y.); or mixtures thereof. A preferred adjuvant comprises ethylene/maleic anhydride copolymer, copolymer of styrene with a mixture of acrylic acid and methacrylic acid, mineral oil emulsion or combinations thereof.

To illustrate examples of how to prepare the FCV-DD1 antigen and make killed FCV-DD1 vaccines, the virus was used to infect confluent CRFK cells at an MOI of 0.01 (typically ranges from about 0.001 to about 1.0) in tissue culture roller bottles. The virus fluids were harvested when 90-100% CPE was observed. The harvested fluids were inactivated with 0.04% formalin at 36° C. for 4 days. Residual formalin was neutralized by the addition of sodium bisulfite. Killed FCV-DD1 vaccines containing approximately 0.5% w/v to approximately 10% w/v of FCV-DD1 were then formulated to contain formalin-inactivated FCV-DD1 alone; FCV-DD1 in combination with killed FeLV (in the amount of approximately 5.0% w/v to approximately 50% w/v), FPV (in the amount of approximately 0.5% w/v to approximately 10% w/v), FCV-255 (in the amount of approximately 0.5% w/v to approximately 10% w/v), FVR (in the amount of approximately 1.0% w/v to approximately 20% w/v) and *C. felis* (in the amount of approximately 0.5% w/v to approximately 10% w/v); and FCV-DD1 in combination with FPV (in the amount of approximately 0.5% w/v to approximately 10% w/v), FCV-255 (in the amount of approximately 0.5% w/v to approximately 10% w/v) and FVR (in the amount of approximately 1.0% w/v to approximately 20% w/v). The vaccines were suitably adjuvanted; and Eagle's minimum essential media were added as the blending diluent. The amount of each antigen in the vaccines was determined using an antigen specific ELISA potency test. The vaccines were found to induce protective immunity against hemorrhagic FCV in standard vaccination challenge tests. The lack of interference of other vaccine fractions from the FCV-DD1 was confirmed by either challenge or serological tests. Another vaccine formulation containing FCV-DD1, FPV, FCV-255, FVR and *C. felis* was also prepared.

Another embodiment of the present invention involves a new method of protecting a feline against infection or preventing disease caused by feline calicivirus that comprises administering to the feline an immunologically effective amount of the vaccines described herein that contain the isolated and purified hemorrhagic feline calicivirus FCV-DD1. Additional methods protect the feline against infection or prevent disease caused by other pathogenic agents using one or more antigens in conjunction with FCV-DD1 such as, for example, feline leukemia virus, feline panleukopenia virus, feline rhinotracheitis virus, feline immunodeficiency virus, rabies virus, feline infectious peritonitis virus, *Bartonella*, etc. and, more preferably, a combination of the antigens encompassing one or more non-hemorrhagic feline caliciviruses such as FCV-255, feline rhinotracheitis virus and feline panleukopenia virus, with the optional addition of feline leukemia virus and/or *C. felis*, or other hemorrhagic FCV strains, comprising the administration to the feline of an immunologically effective amount of the multivalent vaccines described herein.

A further embodiment of the present invention is drawn to the antibodies that are raised or produced against the FCV-DD1 antigen. The antibodies may be raised or produced either by in vitro or in vivo methods that are well known to those of ordinary skill in the art. For example, a typical in vivo method to stimulate the formation of antibodies against FCV-DD1 comprises directly administering to the feline an immunologically effective amount of FCV-DD1 or an antigenic subunit thereof that will be sufficient to induce detectable virus-neutralizing antibody titers. Both monoclonal antibodies specific for the FCV-DD1 antigen and polyclonal antibodies useful to recognize different epitopes of the hemorrhagic calicivirus strains closely related to the FCV-DD1 antigen may be used in the practice of this invention. Further methods of this invention are based on antigen-antibody interaction and the ability of the FCV-DD1 antigen and anti-FCV-DD1 antibodies to form a detectable immune complex. Such methods include a method of detecting or diagnosing a hemorrhagic feline calicivirus infection in a susceptible host which comprises analyzing a biological specimen from the host and detecting the presence of FCV-DD1 or an antibody raised or produced against FCV-DD1 in the biological specimen and a method of detecting the anti-FCV-DD1 antibody in a biological sample which comprises contacting the biological sample with an antigen comprising FCV-DD1 and detecting or observing the formation of an antigen-antibody immune complex. The antigen used in these methods is, for example, the whole virus FCV-DD1, an antigenic subunit of FCV-DD1 such as the immunogenic capsid protein and the like.

An additional method of the present invention to detect a carrier of the hemorrhagic feline calicivirus is warranted because the virus is highly contagious and virulent. The infectious FCV can be carried or transmitted by an asymptomatic cat to other cats, or caretakers in a hospital setting can easily spread the infection from sick cats shedding the virus to healthy cats. Therefore, a method of detecting the carrier of the hemorrhagic feline calicivirus is presented that involves the steps of (a) obtaining a test sample from asymptomatic cats (urine, serum, sputum, feces, etc.), caretakers or pet owners (cat hairs from clothes, hands, furniture, etc.), cat cages and the like; (b) incubating the test sample with an antibody specific to FCV-DD1; (c) allowing the formation of an antibody-antigen complex; and (d) detecting the presence of the antibody-antigen complex. This invention further contemplates other comparable methods making use of the specific antigen-antibody interaction that will be apparent to those of ordinary skill in the art.

The antigen-antibody immune complex may be detected by any standard immunoassay that includes, but is not limited to, enzyme-linked immunosorbent assay (ELISA), Western Blot, immunohistochemistry, flow cytometry and the like. Well-known flow cytometry techniques, for instance, can use a device such as a Becton-Dickinson FACScan Flow Cytometer that detects and measures the amount of fluorescent dye on particles. A sample cell or specimen is labeled with a fluorochrome-labeled antibody, excess unbound antibody is washed off, and then the sample is analyzed by the flow cytometer. The degree of fluorescence and laser-scatter indices are observed and recorded for the sample cells passing through the cytometer. In this fashion, the displayed data in the form of color histograms showing the relationship between the fluorochrome and light scatter characteristic confirms the presence of bound FCV-DD1 antigen in the sample.

Other standard in vitro immunological assays for detection of viral specific antibodies in serum or other test samples may be used through direct or indirect immunofluorescent methods of antibody detection and titer determination. Indirect immunofluorescent assays may be used to screen and identify FCV in a sample specimen. For example, a test sample is incubated with FCV-DD1 antigen, a fragment of the major capsid protein unique to FCV-DD1 in which the fragment can be a synthetic peptide or a short peptide chain expressed using recombinant DNA techniques, related hemorrhagic calicivirus isolates and the like, then coated and stabilized on a glass slide. If anti-FCV-DD1 antibodies are present in the sample, a stable antigen-antibody immune complex forms. The bound antibody is then reacted with a fluoroescein-conjugated reactant and the complex is observed with a fluorescence microscope. A brightly colored fluorescence at the antigen site confirms the positive antibody reaction. Other standard ELISA or immunochromatography techniques may be employed for diagnostic purposes in the detection of antibodies or antigens coupled to an easily-assayed enzyme such as, for example, detection of the presence of FCV-DD1 antigens that are recognized by a monoclonal antibody or test for antibodies that recognize the FCV-DD1 antigen. ELISAs, in particular, can supply a useful measurement of either antigen or antibody concentrations. Alternatively, the FCV-DD1 antigen may be attached to a solid support such as a polystyrene surface of a microwell test strip. The test sample such as cat serum is washed to remove residual serum and then peroxidase-conjugated enzyme is added. A detectable substrate such as the colorless tetramethylbenzidine/hydrogen peroxide is also added and hydrolyzed by the enzyme. The chromogen changes to a blue color. After the reaction is stopped with the addition of acid, the colorless tetramethylbenzidine/hydrogen peroxide changes to yellow. In the final analysis, the intensity of the color detects the presence of the antibody-antigen complex in the sample.

The new FCV strain has been deposited under the conditions mandated by 37 C.F.R. §1.808 and maintained pursuant to the Budapest Treaty in the American Type Culture Collection (ATCC), 10801 University Boulevard, Manassas, Va. 20110-2209, U.S.A. Specifically, the FCV-DD1 sample has been deposited in the ATCC on Sep. 9, 2004 and has been assigned ATCC Patent Deposit Designation PTA-6204.

The following examples demonstrate certain aspects of the present invention. However, it is to be understood that these examples are for illustration only and do not purport to be wholly definitive as to conditions and scope of this invention. It should be appreciated that all scientific and technological terms used herein have the same meaning as commonly understood by those of ordinary skill in the veterinary and pharmaceutical arts. For purposes of this invention, any reference in the specification or the claims to the FCV-DD1 strain includes the viral clones derived from the FCV-DD1 isolate. These viral clones may be readily substituted for FCV-DD1 in all aspects of the vaccines, methods, etc. described herein. It should be further appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless specified otherwise.

A further understanding of the invention may be obtained from the non-limiting examples that follow below.

Example 1

Failed Attempt to Isolate Hemorrhagic Feline Calicivirus

Two 25-$cm^2$ tissue culture flasks of FCV-Ari (labeled 1:100 and 1:1000) were obtained from Dr. Neils Pedersen, School of Veterinary Medicine, UC Davis (N. C. Pedersen et al, "An isolated epizootic of hemorrhagic-like fever in cats caused by a novel and highly virulent strain of feline calicivirus," Veterinary Microbiol. 73:281-300 (May 2000)). The FCV-Ari flask labeled 1:1000 was frozen and thawed. Then 1 mL of the culture fluid was used to infect one 850-$cm^2$ tissue culture roller bottle of confluent Crandell Feline Kidney Cells (CRFK) (R. A. Crandell et al., "Development, characterization, and viral susceptibility of a feline (*Felis catus*) renal cell line (CRFK)," *In Vitro* 9:176-185 (1973)). Sixteen hours later, the roller bottle was frozen, thawed, and aliquoted as a working stock.

The initial FCV-Ari "working stock" was used to inoculate cats in order to confirm that the material contained hemorrhagic calicivirus. The cats inoculated with the FCV-Ari "working stock" elicited extreme clinical signs such as high pyrexia, edema, dehydration, and death. Thus, the FCV-Ari "working stock" was confirmed to contain the hemorrhagic calicivirus.

The FCV-Ari "working stock" was diluted to a titer of approximately $10^5$ $TCD_{50}$ per mL and 0.2 μm filtered. The filtered FCV-Ari was used for purification/isolation of the most virulent calicivirus strain. The filtered FCV-Ari was serially diluted and used to infect 24-well tissue culture plates confluent with CRFK cells. The well of the highest dilution which displayed a cytopathic effect (CPE) on the CRFK cells was harvested, frozen, quick-thawed, serially diluted, and used to infect another 24-well tissue culture plate confluent with CRFK cells. This procedure was repeated two times for a total of three rounds of purification and isolation.

The purified FCV-Ari was formalin inactivated and used to blend a killed, monovalent vaccine. This FCV-Ari (killed) vaccine was put into cats to measure the serological response to vaccination. The vaccine did not induce virus-neutralizing antibody titers although antibodies against the virus were induced as confirmed by ELISA.

Specifically, the study with the purified, killed FCV-Ari vaccine used 20 cats, five cats per group in doses of 0.5% v/v, 2% v/v and 8% v/v with five controls (no injections). Each of the fifteen cats received 2×1 mL doses subcutaneously at the nape of the neck three weeks apart. At one and two weeks following the final vaccination, there were no measurable serum neutralization (SN) titers to FCV at a time when FCV SN titers are typically at their peak.

To re-test and confirm initial findings, four more cats received 2×1 mL doses three weeks apart with de purified, killed FCV-Ari vaccine. One week following the final vaccination, there were no measurable serum neutralization antibody titers (all <2) at the timepoint when serum neutralization titers for FCV are typically the highest.

The purified FCV-Ari (live) was also used to inoculate two groups of cats. The two groups of cats exhibited no clinical signs characteristic of a hemorrhagic calicivirus infection such as high temperatures, edema, pyoderma, alopecia, etc. Therefore, it was confirmed that the strain purified from the "working stock" was not the hemorrhagic calicivirus strain.

Because the vaccine also did not induce neutralizing antibodies, further work and development of this strain ceased.

Example 2

Isolation of FCV-DD1 by Limiting Dilution Cloning

The original FCV-Ari received from Dr. Pedersen, labeled 1:100, was used for three rounds of limiting dilution cloning to purify and isolate FCV-DD1. The FCV-Ari 1:100 sample was incubated with the antisera generated from the original FCV-Ari (killed) vaccination to neutralize the FCV strain isolated from the first purification/isolation of FCV-Ari. The virus was serially diluted and used to infect 24-well tissue culture plates confluent with CRFK cells and the well of the highest dilution which showed a cytopathic effect (CPE) on the CRFK cells was harvested, frozen, and quick thawed. The harvested clones were evaluated by serum neutralization assays. (For a general description of the limiting dilution cloning method and serum neutralization assays used for distinguishing and isolating FCV strains, see H. Poulet et al., "Comparison between acute oral/respiratory and chronic stomatitis/gingivitis isolates of feline calicivirus: pathogenicity, antigenic profile and cross-neutralisation studies," Arch. Virol. 145:243-261 (2000).) Each viral clone of FCV-A was incubated with the antisera generated from the first purification killed vaccine, or with the antisera generated from challenge with the live "working stock." The results from this serum neutralization assay showed that there was more than one strain of calicivirus in the original sample. The viral clones that were not selected and discarded were those that were neutralized by the antisera specific to the undesired product of the first purification. The virus clones selected for the subsequent rounds of purification were those that were neutralized by antisera to the original virus sample from Dr. Pedersen yet were not neutralized by antisera specific to the undesired product of the first purification. This pattern of virus clone selection, harvesting the highest dilution containing CPE, was repeated for a total of three rounds. The resulting clone, designated FCV-DD1, was chosen for biological studies.

Specifically, the FCV-Ari sample was neutralized and repurified through limiting dilution cloning. To neutralize the FCV-Ari virus, the original tissue culture of FCV-Ari sample was diluted to 1:200 in 1×MEM (modified Eagle's medium). The antisera generated from the original FCV-Ari (killed) vaccination (Vaccinate α-Ari serum) was diluted 1:50 in 1×MEM. To 2 mL of diluted anti-Ari serum was added 2 mL of diluted virus. The virus/antisera mixture was incubated for about 1 hour at 37° C.

From a pilot FCV-Ari purification using neutralized virus, it was found that the CPE in 24-well plates was positive up to $10^{-2}$ dilution ($10^{-2}$ wells were 50% CPE and $10^{-3}$ were 0% CPE). Based on this information, the virus was diluted to achieve CPE in about 50% of the wells of CRFK cells. Three dilutions were done, over the goal by fourfold, at the goal and under the goal by fourfold.

One 24-well plate was used for each dilution. All 24 wells were used as replicates of the same dilution. These plates were incubated at 37° C. with 5% $CO_2$ for 4 days. Wells which were positive for CPE in the dilution that gave less than or approximately equal to 50% CPE in the 24 replicates (i.e., ≤12 positive wells) were harvested.

For Round #1 of the limiting dilution cloning procedure, cross neutralization analysis was performed on the harvested clones. Each harvest was diluted 1:200 and 1:1000 in 1×MEM and mixed with dilutions of either Challenge α-Ari (antiserum generated from challenge with the live "working stock") or Vaccinate α-Ari (antiserum from the first purification killed vaccine), in replicates of two. The virus-serum mixture was incubated at 37° C. for 1 hour and then plated onto CRFK cells in 96-well plates. The plates were incubated for 3 days and read for CPE. Results from the first round of limiting dilution cloning and cross neutralization screening are shown in the below Table 1.

Five harvested clones (AB2, BC1, BC4, CB4 and DD1) were neutralized by antisera to the original virus sample from Dr. Pedersen yet were not neutralized by antisera specific to the undesired product of the first purification. They were selected for Round #2 of purification.

For Round #2 of the limiting dilution cloning procedure, the CPE in 24-well plates was found to be positive up to $10^{-5}$ to $10^{-6}$. Three dilutions were done, over the goal by fourfold, at the goal and under the goal by fourfold. One 24-well plate was used for each dilution. All 24 wells were used as replicates of the same dilution. These plates were incubated at 37° C. with 5% $CO_2$ for 4 days. Wells that were positive for CPE in the dilution that gave ≤50% CPE in the 24 replicates were harvested.

The above steps were repeated for the third round of limiting dilution cloning.

TABLE 1

FCV-Ari Limiting Dilution Cross Neutralization Screening

| Harvest ID | Virus Dilution | Challenge α-Ari | Vaccinate α-Ari |
|---|---|---|---|
| AB2 | 1:200 | >256 | <2 |
| AB2 | 1:1000 | >256 | <2 |
| BC1 | 1:200 | >256 | <2 |
| BC1 | 1:1000 | >256 | <2 |
| BC4 | 1:200 | >256 | <2 |
| BC4 | 1:1000 | >256 | <2 |
| CA4 | 1:200 | >256 | <2 |
| CA4 | 1:1000 | >256 | <2 |
| CB2 | 1:200 | >256 | <2 |
| CB2 | 1:1000 | >256 | <2 |
| CB3 | 1:200 | >256 | <2 |
| CB3 | 1:1000 | >256 | <2 |
| CB4 | 1:200 | >256 | <2 |
| CB4 | 1:1000 | >256 | <2 |
| CC5 | 1:200 | >256 | <2 |
| CC5 | 1:1000 | >256 | <2 |
| CD1 | 1:200 | >256 | 37 |
| CD1 | 1:1000 | >256 | <2 |
| DA5 | 1:200 | >256 | <2 |
| DA5 | 1:1000 | >256 | <2 |
| DB1 | 1:200 | >256 | <2 |
| DB1 | 1:1000 | >256 | <2 |
| DB5 | 1:200 | >256 | <2 |
| DB5 | 1:1000 | >256 | <2 |
| DC2 | 1:200 | >256 | <2 |
| DC2 | 1:1000 | >256 | <2 |
| DD1 | 1:200 | >256 | <2 |
| DD1 | 1:1000 | >256 | <2 |
| DD2 | 1:200 | >256 | <2 |
| DD2 | 1:1000 | >256 | <2 |
| DD4 | 1:200 | >256 | <2 |
| DD4 | 1:1000 | >256 | <2 |

Example 3

Isolation of FCV-DD1 Strain

The one harvested clone, DD1, was selected from round #3 and used to infect 850 $cm^2$ tissue culture roller bottle of confluent CRFK cells at MOI (Multiplicity of Infection) of approximately 0.003. The virus fluid was harvested from the roller bottle when 100% CPE was observed, frozen at −50° C. for 4 hours and ten quick thawed in 37° C. water bath. The virus fluid was centrifuged in a Beckman GS-6R Centrifuge (commercially available from Beckman Instruments, Inc., Fullerton, Calif.) at 3000 rpm for 20 minutes, and the cell-free supernatant was aliquoted into 81×1 mL sample vials and stored at −80° C.

Example 4

Physiological Challenge Studies

The isolated and purified FCV-DD1 strain prepared in Example 3 was inoculated into cats. One challenge group of three cats were used wherein each cat received 6.3 logs of virulent FCV-DD1 by administration of 0.25 mL per nostril and 0.5 mL orally for a total of 1 mL. The cats exhibited typical hemorrhagic calicivirus clinical signs. Extremely high temperatures appeared in all 3 cats after 1 day. The edema (swelling) started on the fifth observation day. Ulcerations, both external and oral, appeared on the sixth observation day. Two-thirds of the cats were euthanized (exanguinated) on the sixth observation day since they had become moribund. The third cat was moribund with failing temperatures on the seventh observation day and the study was ended. The results from this challenge study prove that the strain of calicivirus purified and isolated from the original FCV-Ari sample, designated FCV-DD1, was a true hemorrhagic feline calicivirus strain.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

What is claimed is:

1. An isolated and purified virus, comprising a derivative of hemorrhagic feline calicivirus FCV-DD1 having ATCC Patent Deposit Designation PTA-6204, wherein said derivative is an attenuated, modified live, inactivated or killed FCV-DD1 calicivirus.

2. An immunogenic composition comprising an immunologically effective amount of the virus of claim 1, or a subunit derivative thereof.

3. The immunogenic composition of claim 2, further comprising a physiologically acceptable carrier or diluent.

4. The immunogenic composition of claim 3, further comprising an immunogenically effective amount of one or more additional attenuated, modified live, inactivated or killed derivatives of feline calicivirus(es), or subunit derivatives thereof.

5. The immunogenic composition of claim 4, wherein the additional feline calicivirus is selected from the group consisting of FCV-255, FCV-2280, FCV-Diva, FCV-Kaos, FCV-Bellingham, FCV-F9, FCV-F4, FCV-M8 and a combination thereof.

6. The immunogenic composition of claim 5, wherein the additional feline calicivirus comprises FCV-255, FCV-2280 or the combination of FCV-255 and FCV-2280.

7. The immunogenic composition of claim 6, wherein the additional feline calicivirus comprises FCV-255.

8. The immunogenic composition of claim 6, further comprising an antigen selected from the group consisting of *Chlamydophila felis*, feline leukemia virus, feline panleukopenia virus, feline rhinotracheitis virus, feline immunodeficiency virus, rabies virus, feline infectious peritonitis virus, *Bartonella* and a combination thereof.

9. The immunogenic composition of claim 8, wherein the antigen comprises the combination of *Chlamydophila felis*, feline leukemia virus, feline panleukopenia virus and feline rhinotracheitis virus.

10. The immunogenic composition of claim 8, wherein the antigen comprises the combination of *Chlamydophila felis*, and feline rhinotracheitis virus.

11. The immunogenic composition of claim 8 wherein the antigen comprises the combination of feline panleukopenia virus and feline rhinotracheitis virus.

12. The immunogenic composition of claim 8 further comprising an adjuvant.

13. The immunogenic composition of claim 12, wherein the adjuvant is selected from the group consisting of saponin, aluminum phosphate, aluminum hydroxide, a surfactant, a polyanion, a polycation, a detergent, a peptide, a metabolizable animal or vegetable oil, a mineral oil, a mineral oil emulsion, an immunomodulator, a polyoxyethylene-polyoxypropylene block copolymer, a copolymer of styrene with a mixture of acrylic acid and methacrylic acid, a *Corynebacterium*-derived adjuvant, a *Propionibacterium*-derived adjuvant, *Mycobacterium bovis* (Bacille Calmette-Guerin), an interleukin, an interferon, a liposome, an iscom adjuvant, a mycobacterial cell wall extract, a synthetic glycopeptide, avridine, Lipid A, dextran sulfate, DEAE-Dextran, carboxypolymethylene, ethylene/maleic anhydride copolymer, an acrylic copolymer emulsion, an animal poxvirus protein, a subviral particle adjuvant, cholera toxin, dimethyldioctadecylammonium bromide and a combination thereof.

14. The immunogenic composition of claim 13, wherein the adjuvant is an ethylene/maleic anhydride copolymer, a copolymer of styrene with a mixture of acrylic acid and methacrylic acid, a mineral oil emulsion or a combination thereof.

15. The immunogenic composition of claim 13, wherein the adjuvant is saponin, a metabolizable animal or vegetable oil selected from the group consisting of squalane and squalene, a detergent, aluminum phosphate, aluminum hydroxide or a combination thereof.

16. The immunogenic composition of claim 8, wherein the physiologically acceptable carrier or diluent comprises saline or Eagle's minimum essential media.

17. The immunogenic composition of claim 8, further comprising a preservative.

18. The immunogenic composition of claim 17, wherein the preservative is selected from the group consisting of thimerosal, neomycin, polymyxin B, amphotericin B and a combination thereof.

19. A method of protecting a feline from development of clinical hemorrhagic calici disease caused by feline calicivirus FCV-DD1 which comprises administering to the feline an immunologically effective amount of the immunogenic composition according to claim 3.

20. A method of protecting a feline from development of clinical hemorrhagic calici disease caused by feline calicivirus FCV-DD1 which comprises administering to the feline an immunologically effective amount of the immunogenic composition according to claim 4.

21. A method of protecting a feline from development of clinical hemorrhagic calici disease caused by feline calicivirus FCV-DD1 which comprises administering to the feline an immunologically effective amount of the immunogenic composition according to claim 6.

22. A method of protecting a feline from development of clinical hemorrhagic calici disease caused by pathogenic feline calicivirus FCV-DD1; and from development of clinical disease caused by at least one other pathogen selected from *Chlamydophila felis*, feline leukemia virus, feline panleukopenia virus, feline rhinotrachetis virus, feline immunodeficiency virus, rabies virus, feline infectious peritonitis virus, *Bartonella* or a combination thereof, comprising administering to the feline an immunologically effective amount of the immunogenic composition according to claim 8, which is effective to protect the feline from development of clinical disease caused by the corresponding pathogen.

23. A method of protecting a feline from development of clinical hemorrhagic calici disease caused by pathogenic feline calicivirus FCV-DD1; and from development of clinical disease caused by at least one other pathogen selected from feline leukemia virus, feline panleukopenia virus, feline rhinotrachetis virus and *Chlamydophila felis* or a combination thereof, comprising administering to the feline an immunologically effective amount of the immunogenic composition according to claim 9, which is effective to protect the feline from development of clinical disease caused by the corresponding pathogen.

24. A method of protecting a feline from development of clinical hemorrhagic calici disease caused by pathogenic feline calicivirus FCV-DD1; and from development of clinical disease caused by at least one other pathogen selected from feline panleukopenia virus, feline rhinotrachetis virus and *Chlamydophila felis* or a combination thereof, comprising administering to the feline an immunologically effective amount of the immunogenic composition according to claim 10, which is effective to protect the feline from development of clinical disease caused by the corresponding pathogen.

25. A method of protecting a feline from development of clinical hemorrhagic calici disease caused by pathogenic feline calicivirus FCV-DD1; and from development of clinical disease caused by at least one other pathogen selected from feline panleukopenia virus and feline rhinotrachetis virus or a combination thereof, comprising administering to the feline an immunologically effective amount of the immunogenic composition according to claim 11, which is effective to protect the feline from development of clinical disease caused by the corresponding pathogen.

26. A method of claim 19, wherein the immunogenic composition is administered parenterally, orally, intranasally, oronasally or transdermally to the feline.

27. The method of claim 26, wherein the immunogenic composition is administered intramuscularly, subcutaneously or oronasally to the feline.

28. The immunogenic composition of claim 2, which is a vaccine.

29. The immunogenic composition of claim 3, which is a vaccine.

30. The immunogenic composition of claim 8, which is a vaccine.

31. The immunogenic composition of claim 30, which vaccine is effective to protect a feline from development of clinical disease caused by the corresponding pathogen.

32. The method of claim 19, where the immunogenic composition is a vaccine.

33. The method of claim 20, where the immunogenic composition is a vaccine.

34. The method of claim 22, where the immunogenic composition is a vaccine.

* * * * *

UNITED STATES PATENT AND TRADEMARK OFFICE

CERTIFICATE OF CORRECTION

PATENT NO. : 8,685,412 B2
APPLICATION NO. : 13/226685
DATED : April 1, 2014
INVENTOR(S) : Chengjin Huang It is certified that error appears in the above-identified patent and that said Letters Patent is hereby corrected as shown below:

On the Title Page, Item (54) Title: reads "HEMORRHAGIC FELINE CALICIVIRUS, CALICIVIRUS VACCINE AND METHOD FOR PREVENTING DEVELOPMENT OF CALICIVIRUS DISEASE", should read --HEMORRHAGIC FELINE CALICIVIRUS, CALICIVIRUS VACCINE AND METHOD FOR PREVENTING CALICIVIRUS INFECTION OR DISEASE--.

Signed and Sealed this
Tenth Day of February, 2015

Michelle K. Lee
*Deputy Director of the United States Patent and Trademark Office*